(12) United States Patent
Codignola

(10) Patent No.: US 7,084,309 B2
(45) Date of Patent: Aug. 1, 2006

(54) PROCESS FOR THE SYNTHESIS OF PHENOL AND ACETONE

(75) Inventor: Franco Codignola, Milan (IT)

(73) Assignee: Eurotecnica Development & Licensing S.p.A., Milan (IT)

( * ) Notice: Subject to any disclaimer, the term of this patent is extended or adjusted under 35 U.S.C. 154(b) by 0 days.

(21) Appl. No.: 10/507,225

(22) PCT Filed: Mar. 14, 2002

(86) PCT No.: PCT/IT02/00156

§ 371 (c)(1),
(2), (4) Date: Apr. 14, 2005

(87) PCT Pub. No.: WO03/076376

PCT Pub. Date: Sep. 18, 2003

(65) Prior Publication Data

US 2005/0177004 A1    Aug. 11, 2005

(51) Int. Cl.
C07C 39/04    (2006.01)

(52) U.S. Cl. .................................................. 568/716

(58) Field of Classification Search ............ 568/385, 568/576, 798, 716
See application file for complete search history.

(56) References Cited

U.S. PATENT DOCUMENTS

| | | | |
|---|---|---|---|
| 3,037,052 A | 5/1962 | Bortnick | 260/485 |
| 4,404,409 A | 9/1983 | Fujiwara et al. | 568/697 |
| 4,898,995 A * | 2/1990 | Knifton et al. | 568/798 |
| 5,245,090 A | 9/1993 | DeCaria et al. | 568/798 |

FOREIGN PATENT DOCUMENTS

EP    0 367 408 A3    5/1990

* cited by examiner

Primary Examiner—Samuel Barts
Assistant Examiner—Kellette Gale
(74) Attorney, Agent, or Firm—Ohlandt, Greeley, Ruggiero & Perle, L.L.P.

(57) ABSTRACT

This invention refers to a process for the synthesis of phenol and acetone starting from cumene hydroperoxide, and to a plant specifically developed for performing this process. More in particular, this invention refers to a process for the synthesis of phenol and acetone starting from cumene hydroperoxide, comprising the following steps: a) Pretreating of the starting cumene hydroperoxide with acidic resins, to obtain cumene hydroperoxide free of inorganic cations; b) Decomposing of the cumene hydroperoxide free of inorganic cations originating from the step (a) in the presence of acidic resins, to yield phenol and acetone.

19 Claims, 1 Drawing Sheet

PROCESS FOR THE SYNTHESIS OF PHENOL AND ACETONE

FIELD OF THE INVENTION

Figure 1:
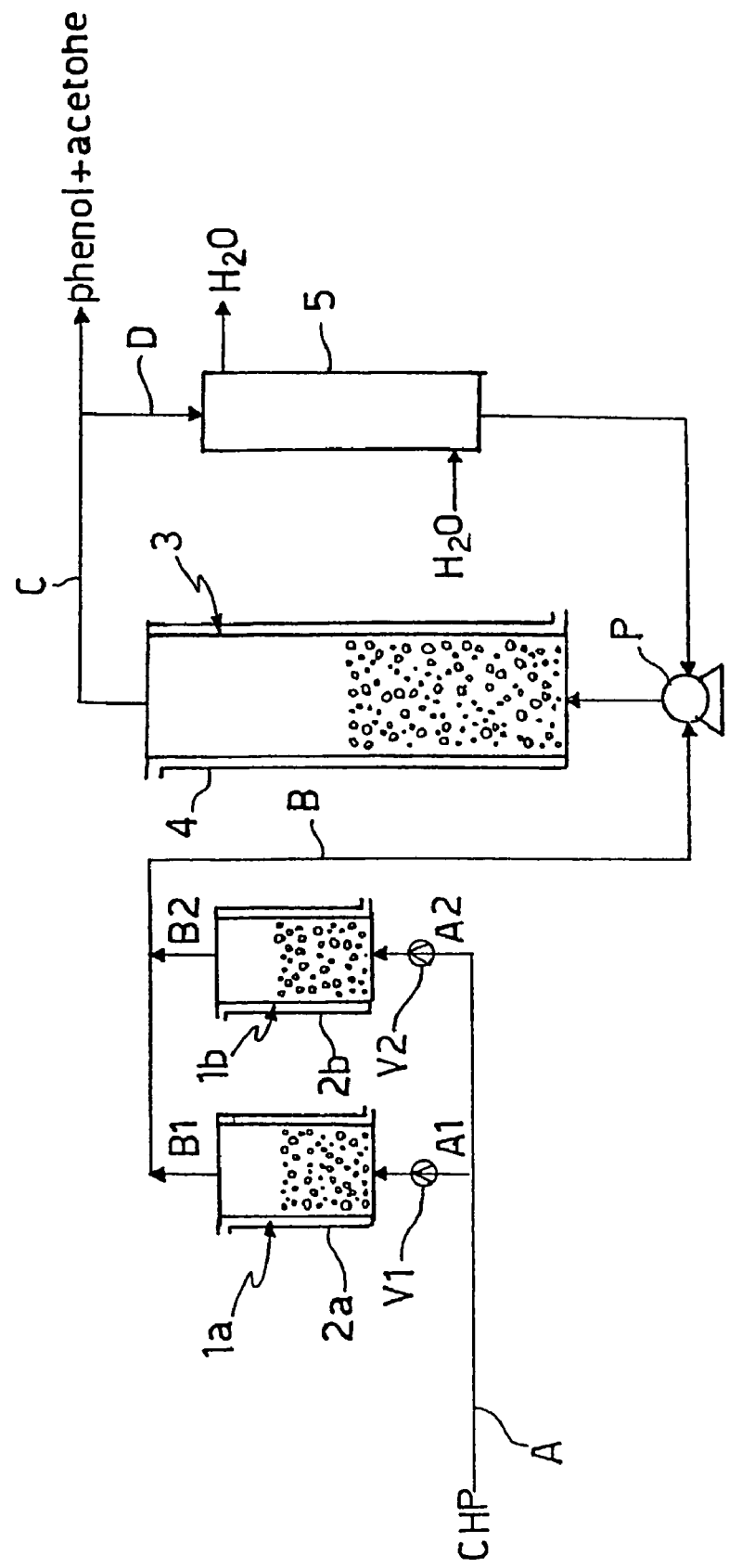

This invention refers to a process for the synthesis of phenol and acetone starting from cumene hydroperoxide.

BACKGROUND ART

As known, the most widely employed industrial process for the synthesis of phenol is that providing for the decomposition of cumene hydroperoxide. At this time, over 90% of the phenol produced in the world is synthesized by this route, which simultaneously yields a mole of acetone per mole of phenol produced in accordance with the following reaction:

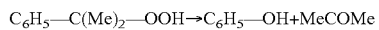

The cumene hydroperoxide is prepared by oxidizing cumene with air in a liquid phase:

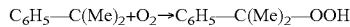

The main byproducts of this reaction are acetophenone, dimethylphenylcarbinol and formic acid.

The latter in particular has, because of its acidity, the capability of catalyzing a partial decomposition of the cumene hydroperoxide to phenol, which even if present in parts per million, blocks the further oxidation of cumene with the result that the reaction is interrupted at an unacceptably low percentage of conversion.

It is known that in order to neutralize the formic acid byproduct aqueous solutions of sodium salts with organic acids are introduced into the cumene mixture so as to buffer the reaction environment. An alternative employed for the same purpose was that of using the sodium salt of the same cumene hydroperoxide under anhydrous conditions (U.S. Pat. No. 3,171,860 in the name of F. Codignola). On the other hand, the process in current use provides for feeding the oxidation reactor with cumene and caustic soda in a concentrated aqueous solution, so as to maintain a pH of an adequately high level to prevent initiating the decomposition of the hydroperoxide.

All the processes of the known art have in common that they utilize bases with inorganic cations (typically sodium, potassium and ammonium). Despite the fact that the reaction mixture exiting the oxidation step is washed with water to remove the salts, the cumene hydroperoxide thus produced still contains a small yet uneliminable percentage of inorganic cations in addition to a residual percentage of water. The presence of such cations is particularly disadvantageous for performing the subsequent decomposing reaction to yield phenol and acetone, as it interferes with the functionality of the acidic resins which could effectively be employed as decomposing catalysts. This consideration has limited the choice of acidic catalysts to traditional inorganic acids, in particular to sulphuric acid. The strong inorganic acids such as sulfuric acid, however, involve considerable safety problems in usage and waste disposal condition.

SUMMARY OF THE INVENTION

The problem underlying this invention is therefore making available a process for the synthesis of phenol and acetone which does not provide for the application of acidic catalysts which are complex and hazardous to use.

This problem is solved by a process for the synthesis of phenol and acetone as outlined in the attached claims.

DETAILED DESCRIPTION OF THE INVENTION

The process of the invention provides for the decomposition of cumene hydroperoxide in the presence of acidic resins as decomposing catalysts, in accordance with the following reaction:

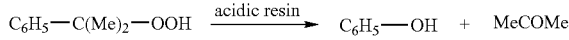

This process comprises the following two steps:
a) Pretreating of the initial cumene hydroperoxide (CHP) with acidic resins, to obtain cumene hydroperoxide free of inorganic cations;
b) Decomposing of the cumene hydroperoxide free of inorganic cations originating from the phase (a) in the presence of acidic resins, to yield phenol and acetone.

The step (a) of pretreating CHP with the acidic resins is preferably performed at such a temperature as not to cause a substantial decomposition of CHP. More preferably, the step (a) will be performed at a temperature below 20° C. Operating under these conditions avoids the need for setting up devices for dissipating heat at the pretreating reactor, which are otherwise needed because of the exothermal nature of the decomposing reaction.

The step (b) of decomposing the cumene hydroperoxide is exothermic and proceeds rapidly to a CHP conversion of about 100%. The temperature during this phase is maintained between 35° C. and 90° C., preferably between 40° and 50° C.

The acidic resin will preferably be employed, both in the CHP pretreating step (a) and in the decomposing step (b), in quantities comprised between 2% and 25%, preferably between 5% and 15% by weight with respect to the hourly flow rate of CHP in each of the pretreating and decomposing reactors, respectively. The quantity of acidic resin will more preferably be about 10% by weight with respect to the hourly flow rate of CHP.

The acidic resin used in the process of this invention will preferably be chosen from ion exchange resins having sulphonic acid (—SO$_3$H) functional groups linked to an organic chain, preferably a polystyrene or styrene-divinylbenzene polymer. Preferred acidic resins are chosen from the group Amberlyst™ 15, Amberlyst™ 18 and Nafion™. The latter in particular is a sulphonic resin with a perfluoridated chain, characterized by high stability to elevated temperatures.

The process of the invention preferably comprises a step (c) of drawing up a portion of the reaction mixture exiting the step (b), a step (d) of cooling said portion of the reaction mixture to a temperature of 35–45° C., more preferably of about 40° C., and a step (e) of recirculating the same to the decomposing reactor. This makes it possible to dilute the cumene hydroperoxide entering the decomposing step (b) with the already reacted product, so as to limit the temperature increase due to the exothermal nature of the reaction. The quantity of product recycled in accordance with the steps (c), (d) and (e) will be comprised between 80% and 95% by weight, preferably about 90% by weight, of the reaction mixture exiting the step (b).

The process of the invention may also comprise a step of regenerating the acidic resin employed in said CHP pretreating step (a). Said acidic resin regenerating step will preferably be performed by treating with a solution of sulphuric acid, for instance with sulphuric acid at 15% by weight. More preferably, the resin may first be washed with water and acetone. Provision may also be made for washing with water after treating with the sulphuric acid solution.

A plant specifically developed for implementing the process of the invention constitutes a further object of this invention.

Such a plant will comprise a CHP decomposing reactor containing a preestablished quantity of acidic resin and set up upstream of such a decomposing reactor, at least one reactor for pretreating the cumene hydroperoxide with said acidic resins. Preferably, at least two reactors will be provided for pretreating CHP with acidic resin, where said at least two pretreating reactors are set up in parallel and operating in an alternating manner. This will in fact make it possible to perform the regeneration of the acidic resin contained in one of the two or more pretreating reactors without a need for interrupting the process. Two pretreating reactors set up in parallel will generally be adequate to ensure the continuity of the process, while in principle not excluding a provision for three or more pretreating reactors. In the above mentioned case of two preatreating reactors, the CHP feeding line will split up into two parallel paths, each passing through a preatreating reactor, which may be mutually excluded.

Downstream of the decomposing reactor, provision will be made for a product discharging line, from which a line will preferably be provided for recirculating the reaction mixture so as to return it the CHP decomposing reactor after crossing the appropriate heat exchanging means. In case a provision is made for such a recirculation of the reaction mixture, the volume of each of the pretreating reactors will be less than the volume of the decomposing reactor by a factor generally proportional to the ratio between the flow rate of the recirculated fluid and the flow rate of the feeding fluid.

The invention will now be further described by an example of an embodiment, as outlined below for indicative and non-limiting purposes, with reference to the following figures:

FIG. 1 shows a simplified block diagram of a plant for implementing the process of this invention.

The cumene hydroperoxide is fed along a line A which splits up into two parallel lines A1, A2 each leading to a pretreating reactor 1a, 1b for the cumene hydroperoxide. Appropriate flow regulating means V1, V2, for instance valve units, allow selecting the operating line, and consequently the reactor 1a or 1b associated with the same, while excluding the other line.

The pretreating reactors 1a, 1b will be equipped with cooling means, for instance a cooling jacket 2a, 2b, and in the reactors the acidic resin will be introduced in a predetermined amount depending on the hourly rate expected in the plant.

The respective tranferring lines B1, B2 for the pretreated cumene hydroperoxide will be derived from said preatreating reactors 1a, 1b, so as to join up in a single charging line B leading to the cumene hydroperoxide decomposing reactor 3. Appropriate pumping means P will take care of moving the fluid mass between the reactors.

The decomposing reactor 3 contain the acidic resin in the appropriate amount and is also equipped with cooling means, in the example with a cooling jacket 4.

A discharge line C conveys the reaction products of the decomposing reactor 3 to a product isolating section set up at a downstream location (not shown). From said discharge line C a line D is derived for recirculating a portion of the reaction mixture, which after crossing a heat exchanger 5, returns the reaction mixture to the pumping means P and from there to the charging line B of the decomposing reactor 3.

The acidic resin used in the pretreating reactors and in the decomposing reactor may be the same, or alternatively different resins may be employed. For instance, it will be possible to use Amberlyst™ 15 or 18 in the pretreating reactors and Nafion™ in the decomposing reactor, where the exothermal nature of the reaction may advise the usage of a high temperature resistant resin.

A particular example of an embodiment of the process of the invention will now be described for purely indicative purposes.

EXAMPLE

This example describes a process implemented in a plant like that shown in FIG. 1.

Cumene hydroperoxide (CHP) having a purity of 93% and containing 16.4 mg of sodium cation per kg of CHP are introduced, at a flow rate of 6 tons/hour, into a pretreating catalyst 1a containing 600 kg of Amberlyst™ 18 ion exchange resin. This reactor is kept at a temperature below 20° C. by a cooling jacket.

The CHP exiting the pretreating reactor 1a is analyzed by atomic absorption, which detects no further trace of a sodium cation. This CHP is then conveyed along the line B into a decomposing reactor 3 containing 6 tons of Amberlist™ 18, after having been mixed with 54 tons/hour of decomposition products recirculated at a temperature of about 40° C., as specified below.

The decomposing reactor 3 is appropriately cooled by a cooling jacket 4, so that the reaction products exiting the reactor have a temperature of about 42° C., despite the exothermic nature of the reaction which may cause the temperature within the reactor to locally build up to 50° C. or more.

These reaction products are discharged, at a flow rate of 60 tons/hour, from the reactor 3 and conveyed toward the recovery unit. A substantial portion of the same, amounting to 54 tons/hour, is instead drawn up, cooled to about 40° C. in a heat exchanging unit 5 and then recirculated to the decomposing reactor, after mixing with fresh CHP (6 tons/hour). The portion of reaction products exiting the reactor at a flow rate of 6 tons/hours is analyzed, evidencing a CHP conversion matching the theoretical value.

The advantages of the process of this invention are evident from the foregoing description.

In essence, the use of the acidic resin in the CHP pretreating step allows eliminating the inorganic cations form the CHP, thus making it possible to perform the decomposing step of the same to yield phenol and acetone by using the acidic resin and therefore under moderate conditions and without generating any residues difficult to dispose of.

The CHP, pretreated as described above to eliminate the inorganic cations, does not cause a saturation of the resin's acidic sites due to said cations in the decomposing reactor. This reactor can therefore operate on a continuous basis, without requiring a regeneration of the resin.

The provision for at least two CHP pretreating reactors allows to operate the process in a continuous manner, stopping one for regenerating the resin while operating the other.

It is evident that only certain particular embodiments of the process of producing phenol and acetone as an object of this invention have been described, which the expert will be capable of providing with all those modifications needed for its adaptation to particular and contingent requirements, without thereby deviating from the scope of protection of this invention.

What we claim is:

1. A process for the synthesis of phenol and acetone starting from cumene hydroperoxide, comprising the following steps with each step performed in a different reactor:
    a) pretreating the starting cumene hydroperoxide with acidic resins, to obtain cumene hydroperoxide free of inorganic cations;
    b) decomposing the cumene hydroperoxide free of inorganic cations originating from the step (a) in the presence of acidic resins, to yield phenol and acetone.

2. A process according to claim 1, wherein said step a) of pretreating cumene hydroperoxide with the acidic resins is performed at a temperature such as not causing a substantial decomposition of cumene hydroperoxide.

3. A process according to claim 1, wherein said step a) of pretreating the cumene hydroperoxide with the acidic resins is performed at a temperature below 20° C.

4. A process according to claim 1, wherein said step b) of decomposing the cumene hydroperoxide is performed at a temperature between 35° C. and 90° C.

5. A process according to claim 1, wherein said acidic resin is employed both in the step (a) of pretreating as in the step (b) of decomposing the cumene hydroperoxide, in amounts between 2% and 25% by weight with respect to the hourly flow rate of cumene hydroperoxide in each of the steps (a) of pretreating and (b) of decomposing, respectively.

6. A process according to claim 5, wherein said acidic resin is employed both in the step (a) of pretreating as in the step (b) of decomposing the cumene hydroperoxide, in amounts between 5% and 15% by weight with respect to the hourly flow rate of cumene hydroperoxide in each of the steps (a) of pretreating and (b) of decomposing, respectively.

7. A process according to claim 6, wherein the amount of acidic resin is about 10% by weight with respect to the hourly flow rate of cumene hydroperoxide.

8. A process according to claim 1, wherein said acidic resin is chosen among ion exchange resins having sulphonic acid functional groups (—$SO_3H$) tied to an organic chain.

9. A process according to claim 8, wherein said acidic resin is a sulfonic resin with a perfluoridated chain.

10. A process according to claim 1, further comprising a step (c) of drawing a portion of the reaction mixture exiting the decomposing step (b) of the cumene hydroperoxide, a step (d) of cooling said portion of the reaction mixture at a temperature of 35° C. to 45° C., and a step (e) of recirculating the same to the decomposing step (b).

11. A process according to claim 10, wherein the amount of product recycled according to steps (c), (d) and (e) is between 80% and 95% by weight.

12. A process according to claim 1, further comprising a regenerating step for the acidic resin used in said step (a) of pretreating the cumene hydroperoxide.

13. A process according to claim 12, wherein said acidic resin regenerating step is performed by treating with a solution of sulphuric acid.

14. The process according to in claim 1, comprising:
    providing a decomposing reactor (3) of the cumene hydroperoxide, containing a pre-established amount of acidic resin;
    providing at least one preatreatment reactor (1a, 1b) of the cumene hydroperoxide with said acidic resins, where said at least one pretreating reactor is set up upstream of said decomposing reactor (3);
    providing recirculating means (D, P) of a portion of the products of the decomposing reaction to said decomposing reactor (3); optionally,
    providing heat exchanging means (5) set up downstream of said decomposing reactor (3) along the recirculating line of said portion of products of the decomposing reaction, optionally,
    providing cooling means of said decomposing reactor (3) and of said at least one pretreating reactor (1a, 1b).

15. The process according to claim 14, comprising the provision of at least two pretreating reactors (1a, 1b) of cumene hydroperoxide with acidic resin, where said at least two pretreating reactors are set up in parallel and operating in an alternating manner.

16. A process according to claim 1, wherein said step b) of decomposing the cumene hydroperoxide is performed at a temperature between 40° C. and 50° C.

17. A process according to claim 1, wherein said acidic resin is chosen among ion exchange resins having sulphonic acid functional groups (—$SO_3H$) tied to a polystyrene or styrene-divinylbenzene polymer.

18. A process according to claim 10, wherein the amount of product recycled according to steps (c), (d) and (e) is about 90% by weight of the reaction mixture exiting from the decomposing step (b).

19. A process according to claim 12, wherein said acidic resin regenerating step is performed by treating with a solution of sulphuric acid at 15% by weight.

* * * * *